US010151726B2

(12) United States Patent
Abu-Salah et al.

(10) Patent No.: US 10,151,726 B2
(45) Date of Patent: Dec. 11, 2018

(54) BIOIMAGING NUCLEIC ACIDS, PROTEINS AND ENZYMES

(71) Applicant: King Saud University, Riyadh (SA)

(72) Inventors: Khalid M Abu-Salah, Riyadh (SA); Salman A. Alrokayan, Riyadh (SA); Abdullah M. I. Mashhour, Riyadh (SA)

(73) Assignee: King Saud University, Riyadh (SA)

( * ) Notice: Subject to any disclaimer, the term of this patent is extended or adjusted under 35 U.S.C. 154(b) by 124 days.

(21) Appl. No.: 14/120,373

(22) Filed: May 14, 2014

(65) Prior Publication Data

US 2014/0339083 A1 Nov. 20, 2014

Related U.S. Application Data

(63) Continuation of application No. PCT/US2011/060667, filed on Nov. 14, 2011.

(51) Int. Cl.
*G01N 27/447* (2006.01)

(52) U.S. Cl.
CPC . *G01N 27/44747* (2013.01); *G01N 27/44721* (2013.01); *G01N 27/44726* (2013.01)

(58) Field of Classification Search
CPC ....... G01N 27/44747; G01N 27/44721; G01N 27/44726; B82Y 35/00; B82Y 40/00
See application file for complete search history.

(56) References Cited

U.S. PATENT DOCUMENTS

| | | | |
|---|---|---|---|
| 5,998,789 | A | 12/1999 | Kovalsky et al. |
| 2005/0112743 | A1 | 5/2005 | Potthoff et al. |
| 2009/0277791 | A1 | 11/2009 | Vu et al. |

OTHER PUBLICATIONS

A. M. Mashour, The biochemical behavior of silicon nanoparticles in gels in the presence and absence of nucleic acids or proteins, King Saud University College of Science, Department of Biochemistry, Oct. 2010.*
Suenaga, E., et al., "Prestaining Method as a Useful Tool for the Agarose Gel Electrophoretic Detection of Polymerase Chain Reaction Products with a Fluorescent Dye SYBR Gold Nucleic Acid Gel Stain", Anal. Sci. Jun. 2005, vol. 21, No. 6, pp. 619-623.

(Continued)

*Primary Examiner* — Maris R Kessel
(74) *Attorney, Agent, or Firm* — Hauptman Ham, LLP

(57) ABSTRACT

Systems and methods for labeling, staining, and bioimaging of nucleic acids, their fragments, proteins, polypeptides and enzymes are described. In one aspect, a percentage concentration agarose gel or polyacrylamide gel is generated with agarose or polyacrylamide powder respectively. Silicon nanoparticles are added to the agarose or polyacrylamide gel at a required concentration via the agarose or polyacrylamide powder or after agarose or polyacrylamide solubilization in a loading buffer. The nucleic acid is added to agarose gel slots and proteins or enzymes are added to polyacrylamide gel slots in the loading buffer. The loading buffer is then electrophoresed in each case for an amount of time, causing the added silicon nanoparticles or the added ethidium bromide (after agarose solubilization) to generate a bound and labeled nucleic acid and their fragments and proteins or enzymes (with silicon nanoparticles only).

1 Claim, 10 Drawing Sheets

(56) References Cited

OTHER PUBLICATIONS

Fernandez-Patron, C., et al., "Double Staining of Coomassie Blue-Stained Polyacrylamide Gels Made by Imidazole-Sodium Dodecyl Sulfate-Zinc Reverse Staining: Sensitive Detection of Coomassie Blue-Undetected Proteins", Anal. Biochem., Jan. 1, 1995, vol. 224, No. 1, pp. 263-269.

International Search Report dated Aug. 14, 2012, for International Application No. PCT/US2011/060667, 3 pages.

* cited by examiner

BIOIMAGING NUCLEIC ACIDS, PROTEINS AND ENZYMES

BACKGROUND

Visualization of nuclear components has introduced new dimensions to the biology of the nucleus and new insights into its chemistry. The most common dye used to make DNA or RNA bands visible for agarose gel electrophoresis is ethidium bromide. It fluoresces under UV light when intercalated into the major groove of DNA (or RNA). In the case of DNA, this is usually double-stranded DNA from PCR'S restriction digests, etc. Single-stranded RNA can also be detected, since it usually folds back base pairing for the dye to intercalate. By running DNA through an ethidium bromide-treated gel and visualizing it with UV light, any band containing more than ~20 ng DNA becomes distinctly visible.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Systems and methods for labeling, staining, and bioimaging of nucleic acids, their fragments, proteins, polypeptides and enzymes are described. In one aspect, a method for bioimaging a nucleic acid, protein or enzyme includes generating a percentage concentration agarose gel or polyacrylamide gel with agarose or polyacrylamide powder respectively. Silicon nanoparticles are added to the agarose or polyacrylamide gel at a required concentration via the agarose or polyacrylamide powder or after agarose or polyacrylamide solubilization in a loading buffer. The nucleic acid is added to agarose gel slots and proteins or enzymes are added to polyacrylamide gel slots in the loading buffer. The loading buffer is then electrophoresed in each case for an amount of time, causing the added silicon nanoparticles or the added ethidium bromide (after agarose solubilization) to generate a bound and labeled nucleic acid and their fragments and proteins or enzymes (with silicon nanoparticles only).

This allows biochemists and other researchers in the various biological and medical fields to examine the electrophoretic proteins and enzyme patterns immediately after finishing their electrophoretic runs, since there is no need to wait for staining with coomassie blue and destaining the excess dye.

BRIEF DESCRIPTION OF THE DRAWINGS

The detailed description is set forth with reference to the accompanying figures, in which the left-most digit of a reference number identifies the figure in which the reference number first appears. The use of the same reference numbers in different figures indicates similar or identical items or features.

DETAILED DESCRIPTION

Overview

Systems and methods for using silicon nanoparticles to bioimage, label, and stain nucleic acids, proteins and enzymes, are described. In one exemplary aspect, silicon nanoparticles (i.e., $Si_{29}H_{24}$), for example, that are 1 nm, 3 nm, 5 nm, and 25 nm in diameter, are used to bind to and to label standard deoxyribonucleic acids (DNA), its fragments genomic DNA, polymerase chain reaction products, DNA strands of different molecular weights, and different types and fragments of ribonucleic acid (RNA). Although these nanoparticles are indicated as being a particular size, different nanoparticle sizes can be substituted without departing from the teachings of this invention. Labeling and staining may be visualized under UV light. Staining is generally stable for several days. These and other aspects of the systems and methods are now described in greater detail in view of the exemplary embodiments of FIGS. 1 through 8.

Exemplary Silicon-Agarose/Ethidium Bromide Agarose Gel Electrophoresis

In one implementation, agarose slab gels were prepared at either 1% or 2.5% concentration in Sigma Tris-acetate-EDTA buffer (TAE) after 10× dilution. The mixture is heated in a microwave oven till complete dissolution of agarose. Agarose solution is cooled then poured in the gel compartment of an electrophoresis apparatus. The gel is allowed to solidify for 5 to 10 minutes. Silicon nanoparticles at the chosen concentration with agarose powder or after agarose solubilization while ethidium bromide is added only after agarose solubilization in buffer. Samples were loaded to gel slots in a loading buffer and electrophoresed for 45 min at 40 mA and 140 volts. Bands were visualized under UV light emitted by a UV lamp or microwave UV-20 and photographed for recording.

Exemplary Visualization of Nucleic Acids on Agarose Slab Gels

Figure 1:
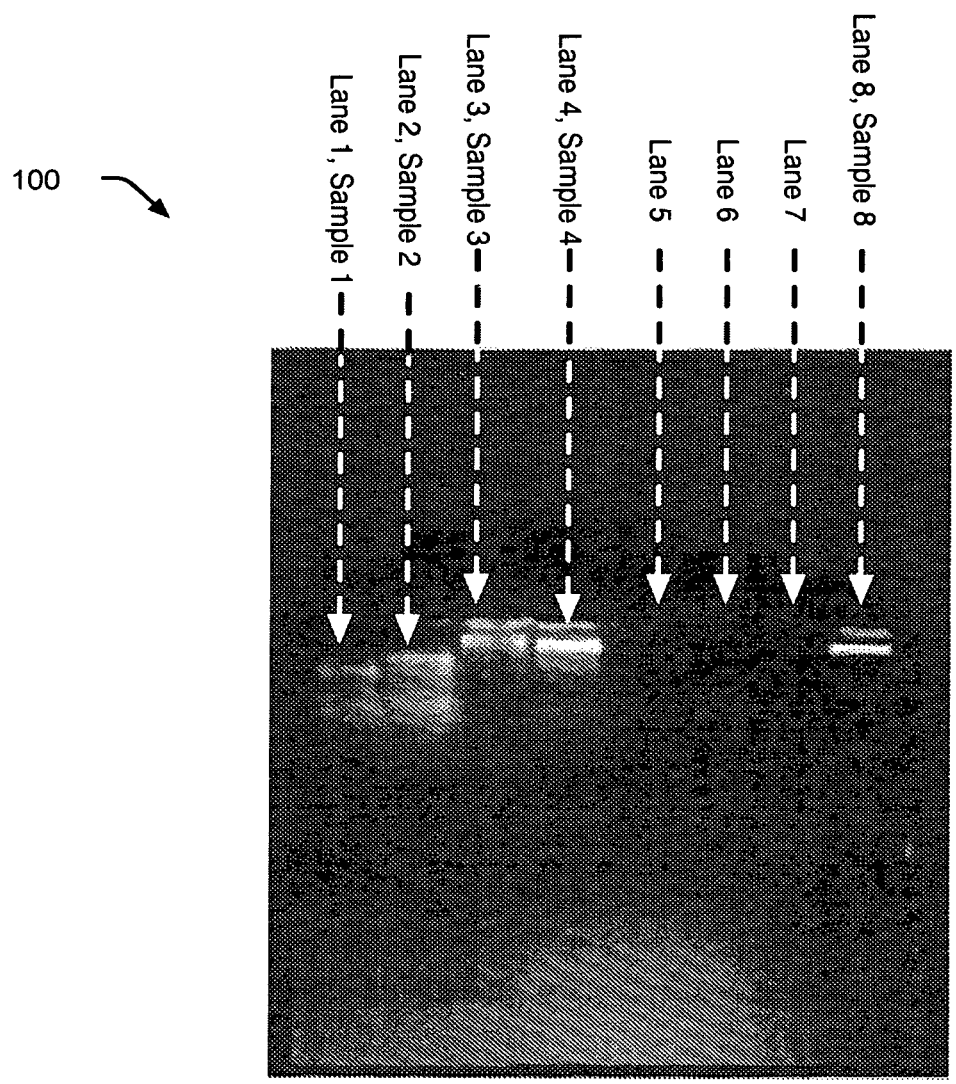
FIG. 1 is an exemplary visualization of standard and genomic DNA on 1% agarose gel in the presence of ethidium bromide according to one embodiment.

FIG. 1 is an exemplary visualization of standard and genomic DNA on 1% agarose gel in the presence of ethidium bromide according to one embodiment. Different types of DNA have been visualized on 1%, 2%, or 2.5% agarose slab gels either in the presence of ethidium bromide or 1 nm silicon nanoparticles. Referring to FIG. 1: samples 1 and 2 are 100 base pair ("bp") DNA ladder (lanes 1 and 2), samples 3 and 4 1000 base pair ("kb") DNA ladder (lanes 3 and 4), lanes 5, 6, and 7 contain only loading dye, lane 8 includes sample 8, which contains genomic DNA.

Figure 2:
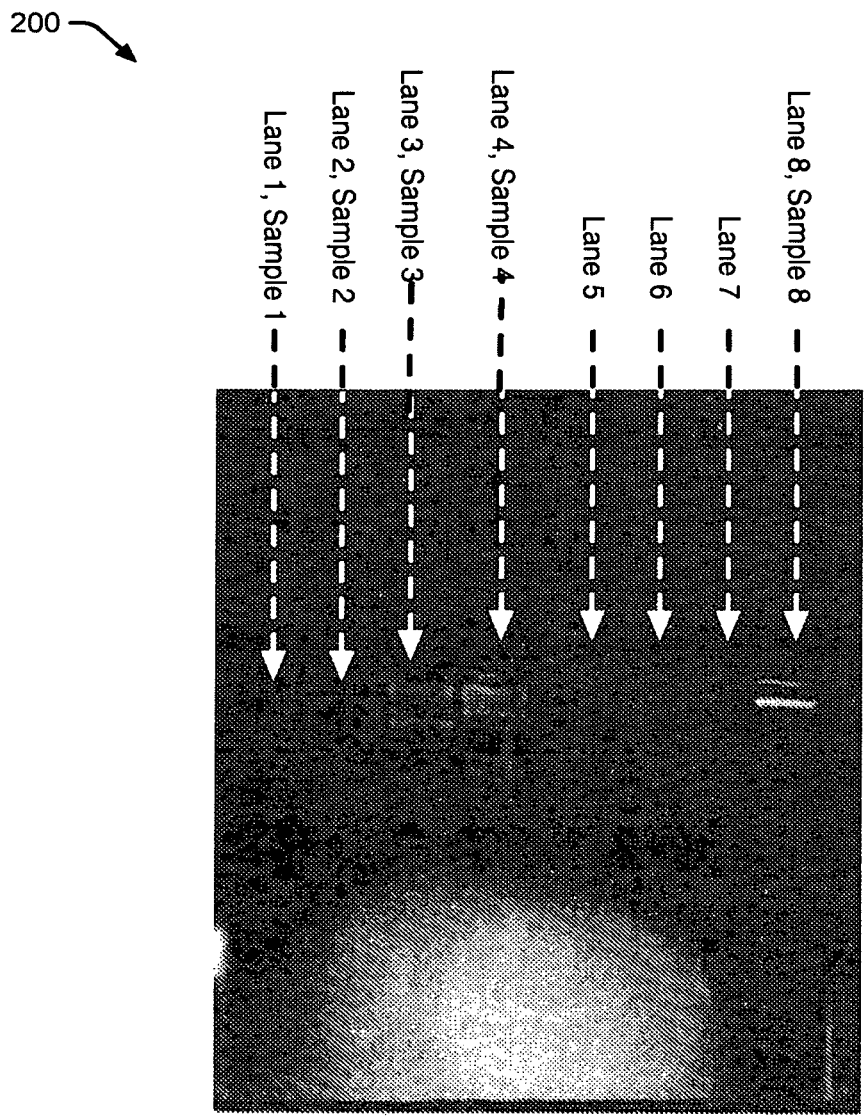
FIG. 2 is an exemplary visualization of standard and genomic DNA on 1% agarose gel in presence of silicon nanoparticles according to one implementation.

FIG. 2 is an exemplary visualization of standard and genomic DNA on 1% agarose gel in presence of 1 nm silicon nanoparticles, according to one implementation. Comparing the bioimaging illustrations on FIG. 1 to those on FIG. 2, show that silicon nanoparticles already embedded in agarose gel are more potent as a staining dye for DNA ladder components and genomic DNA than ethidium bromide (FIG. 2). This is because more minor bands appear especially with 1 KB DNA ladder. As illustrated in FIG. 2, samples 1 and 2 are 100 bp DNA ladder, samples 3 and 4 are 1000 bp DNA ladder, and lanes 5, 6 and 7 contain a loading dye only. Lane 8 contains a sample 8 that is genomic DNA. As discussed below, the same result was obtained when comparing FIGS. 3 and 4, where 2.0% agarose was used as a fractionation medium.

Figure 3A:
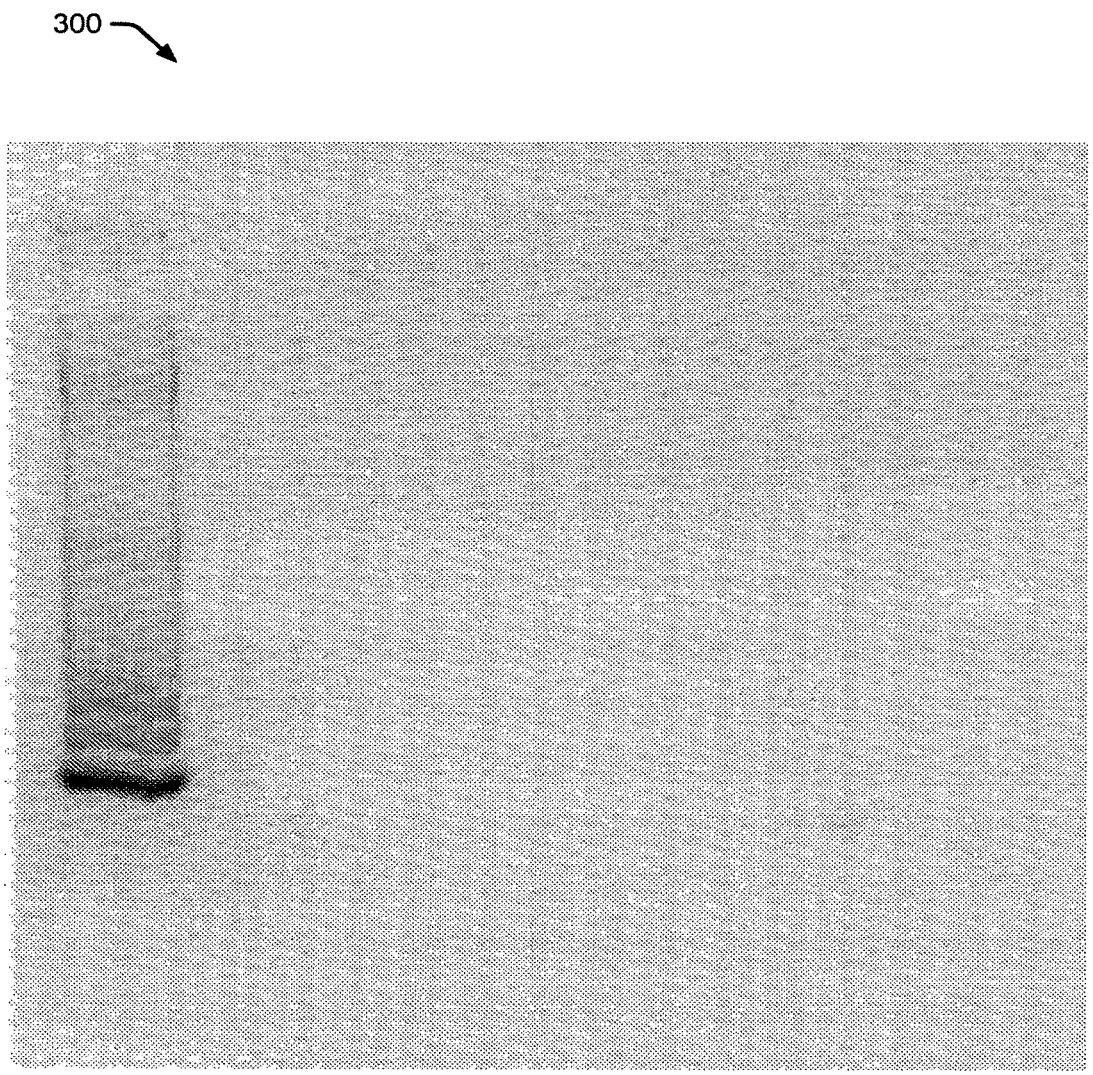
FIG. 3*a* illustrates an exemplary visualization of a standard 100 bp DNA on 2.0% agarose gel in presence of ethidium bromide, according to one embodiment.

FIG. 3a illustrates an exemplary visualization of a standard 100 bp DNA on 2.0% agarose gel in presence of ethidium bromide, according to one embodiment. Referring to FIG. 3a, sample 1 is 100 bp DNA ladder.

Figure 3B:
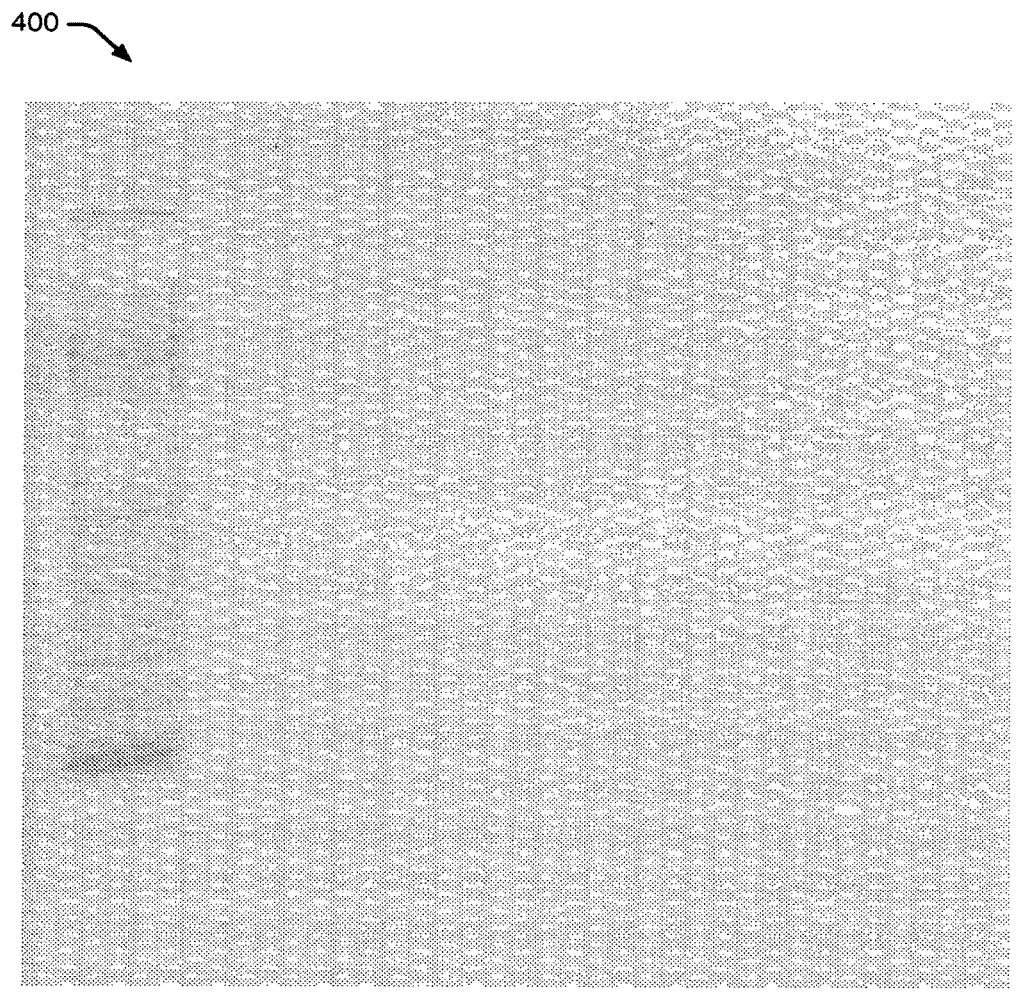
FIG. 3*b* shows an exemplary visualization of a standard 100 bp DNA on 2.0% agarose gel in presence of 1 nm silicon nanoparticles, according to one embodiment.

FIG. 3b shows an exemplary visualization of a standard and genomic DNA on 2.0% agarose gel in presence of 1 nm silicon nanoparticles, according to one embodiment. In FIG. 3b, sample 1 is a 100 bp DNA ladder. In reference to these figures, all DNA ladder components were strongly labeled or stained with silicon nanoparticles in FIG. 3b, while only a few bands appeared when labeling/staining was carried with ethidium bromide, as shown in FIG. 3a.

Figure 4A:
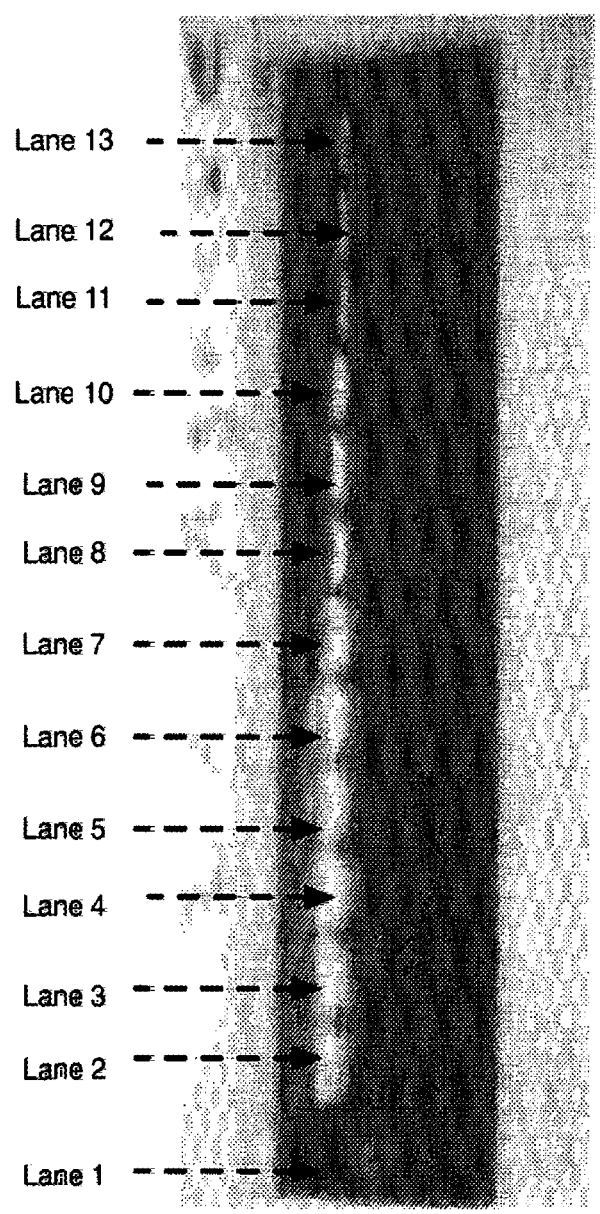
FIGS. 4*a* and 4*b* illustrate exemplary visualization of different amounts of genomic DNA on 1% agarose slab gels, according to one embodiment.
Figure 4B:
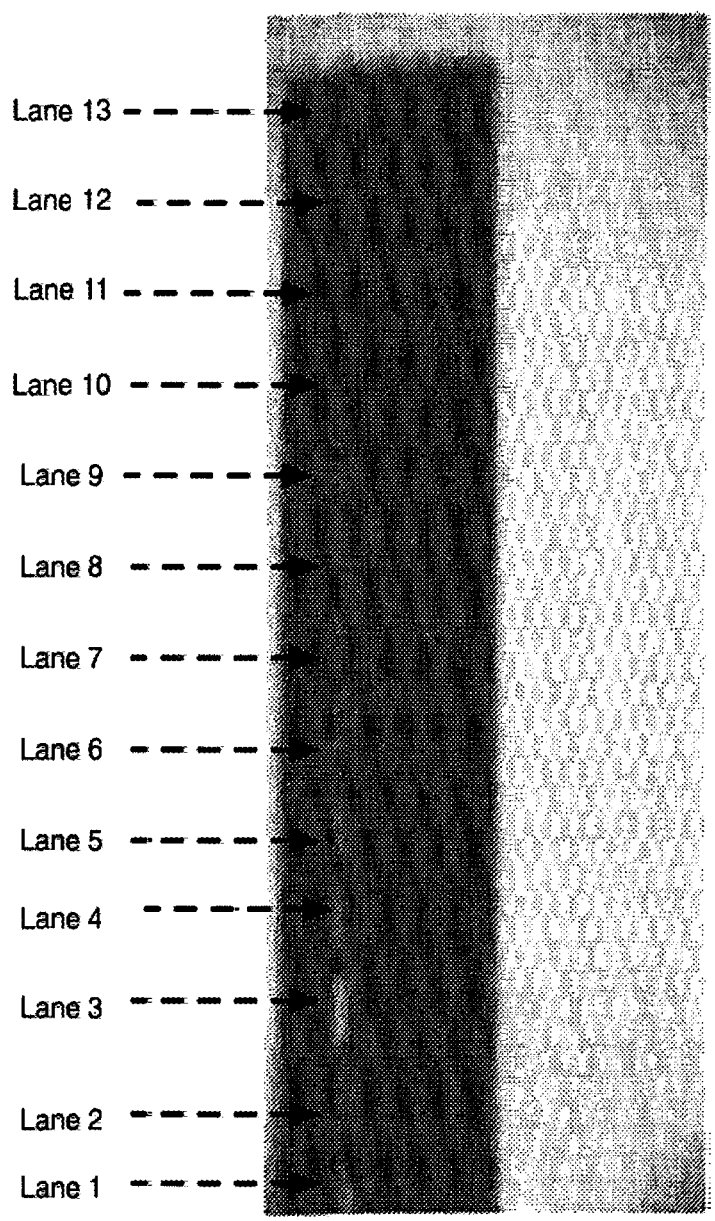

FIGS. 4a and 4b illustrate exemplary visualization of different amounts of genomic DNA on 1% agarose slab gels, according to one embodiment. Referring to FIGS. 4a and 4b, silicon nanoparticles and ethidium bromide demonstrated comparable DNA detection level in the range investigated (400 nanograms ("ng")-4 micrograms ("µg"). Referring to FIG. 4a, this is accomplished in presence of ethidium bromide 4 µg (lanes 2-4), 2 µg (lanes 5-7) and 800 ng (lanes 8-10), 400 ng (lanes 11-13). Referring to FIG. 4b, this is accomplished in presence of 1 nm silicon nanoparticles; 4 µg (lanes 2-4), 2 µg (lanes 5-7) and 800 ng (lanes 8-10), 400 ng (lanes 11-13). Lane 1 contains a 100 bp DNA ladder in both cases.

Figure 5:
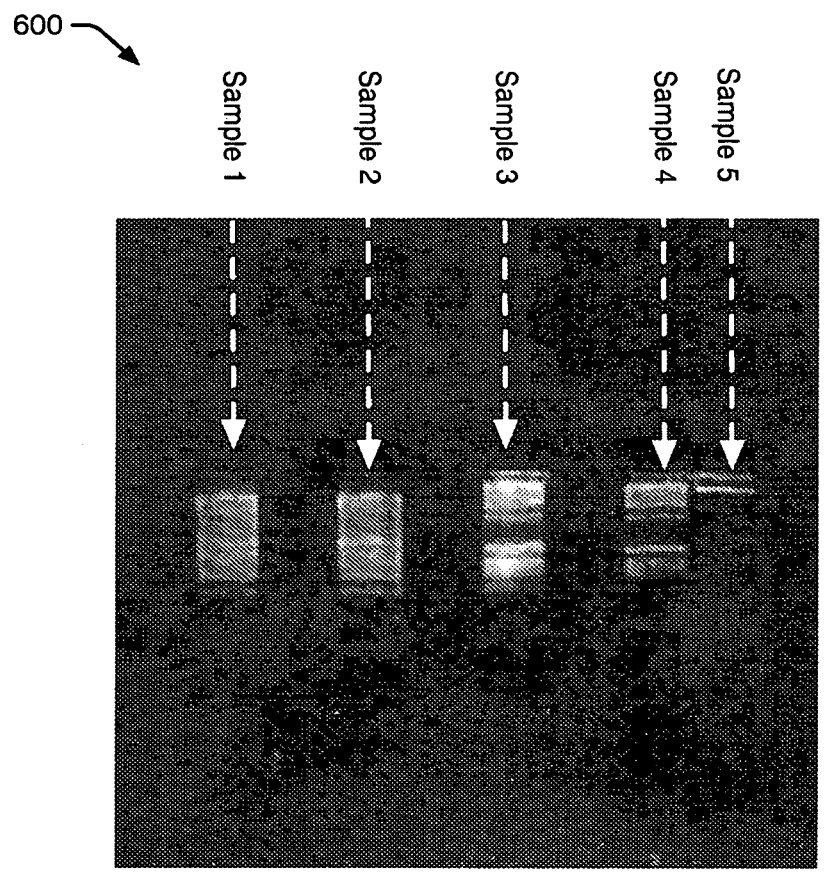
FIG. 5 illustrates an exemplary visualization of standard 100 bp and 1000 bp DNA on 2.5% agarose gel in presence of 1 nm silicon nanoparticles, according to one embodiment.

FIG. 5 illustrates an exemplary visualization of standard and genomic DNA on 2.5% agarose gel in the presence of 1 nm silicon nanoparticles according to an embodiment. Referring to FIG. 5: samples 1 and 2 are 100 bp DNA ladder; samples 3 and 4 are 1000 bp DNA ladder, and sample 5 contains genomic DNA.

Exemplary Visualization of Proteins and Enzymes on Polyacrylamide Gels: SDS-Polyacrylamide Gel Electrophoresis (PAGE)

Figure 6:
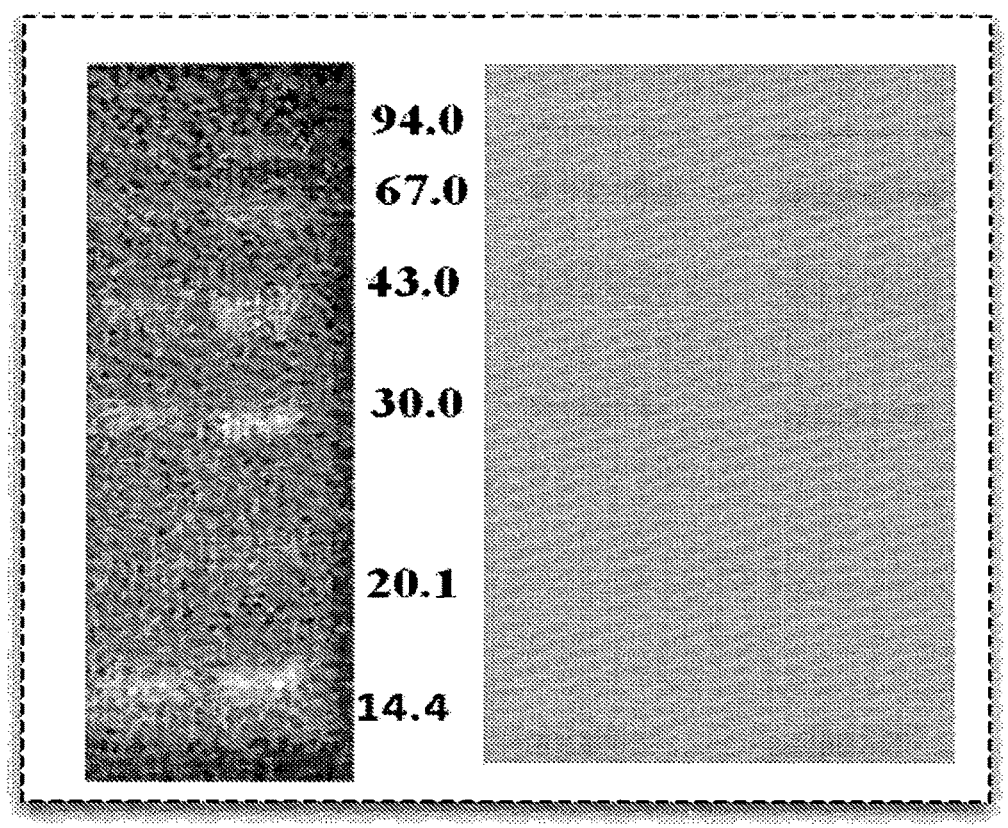
FIG. 6 illustrates an exemplary electrophoretogram of proteins and enzymes on polyacrylamide gel, according to one embodiment.

Different types of proteins and enzymes have been visualized on 12.5% Sodium dodecyl sulfate (SDS) polyacrylamide gel, either with using commassie blue as a staining dye or with using 1 nm silicon nanoparticles. FIG. 6 shows clearly that silicon nanoparticles mixed with polyacrylamide solutions before their gelation can label proteins and enzymes upon subjecting these to electrophoresis. Labeling of protein and enzymes is evident by the fluorescence they emit upon their exposure to ultra violet (UV) light. The fluorescence of each protein or enzyme band indicates the position and its molecular weights in the slab gel are subjected to electrophoresis. The electrophoretic pattern obtained by staining proteins and enzymes with silicon nanoparticles is comparable to that obtained by staining with coomassie blue.

More specifically, sodium dodecyl sulfate polyacrylamide gel electrophoresis (SDS-PAGE) gel is composed of separating and stacking gel. In one exemplary implementation, SDS-PAGE was carried out, in part, as described by the user manual of Hoefer Mighty Small II-Pharmacid Biotech. More particularly, 12.5% Polyacrylamide separating gel was prepared in 0.375M Tris-HCl containing 0.1% SDS weight (of solute) per volume (of solvent) ("w/v"), 0.05% w/v ammonium persulphate and 0.03% volume (of solute) per volume (of solvent) ("v/v") TEMED, pH 8.8. One (1) nm silicon nanoparticles were added in methanol at (976 µg/ml gel mix) (1.16 µmol/ml) (which is equivalent to 1.16 mM). The mixture was poured between the two glass plates of the western blot apparatus. When the gel had set, stacking gel was poured on the top of the separating gel. 4% stacking gel was prepared in 0.125M Tris-HCl, containing 0.1% SDS w/v, 0.05% w/v ammonium persulphate and 0.05% tetramethylethylenediamine (TEMED), pH 6.8. A comb was placed immediately on the stacking gel to form the protein sample wells. The gel was then allowed to set for approximately 20 minutes at room temperature (e.g., 68°).

After the stacking gel has set, the comb was carefully removed and the apparatus was placed in the electrophoresis tank, in which the gel is covered with a running buffer (25 mM Tris-HCl, 192 mM Glycine, 0.1% SDS, pH 8.3). A mixture of standard proteins and enzymes with varying molecular weights were diluted with equal volume of a sample treatment buffer (0.125M Tris-HCl, 4% SDS, 20% glycerol, 2% 2-mercaptoethanol, 0.03 mM bromophenol blue, pH 6.8. Gels were run at 15 mA, till the tracking dye entered the separating (resolving) gel, then for one and a half hour at 20 mA.

Gels where silicon was absent were stained with a coomassie stain solution (e.g., 0.025% Coomassie Blue R-250, 40% methanol in 7% acetic acid). Excess dye was washed out with a destaining solution (40% methanol in 7% acetic acid). Protein bands in gels where silicon is present were visualized under UV light emitted by a UV lamp or microwave UV-20 then photographed, as described above.

Exemplary Visualization of Proteins and Enzymes on Polyacrylamide Gels

FIG. 6 illustrates an exemplary electrophoretogram of proteins and enzymes on polyacrylamide gel, according to one embodiment. As illustrated by this figure, the systems and methods described herein have been used to visualize different types of proteins and enzymes on 12.5% SDS-polyacrylamide gel, either with using coomassie blue as a staining dye (on the right) or with using 1 nm silicon nanoparticles (on the left). FIG. 6 clearly shows that silicon nanoparticles mixed with polyacrylamide solutions before their gelation can label proteins and enzymes upon subjecting these to electrophoresis. Labeling of protein and enzymes is evident by the fluorescence they emit upon their exposure to UV light. The fluorescence of each protein or enzyme band indicates the position and its molecular weights in the slab gel are subjected to electrophoresis. The electrophoretic pattern obtained by staining proteins and enzymes with silicon nanoparticles is comparable to that obtained on the right by staining with coomassie blue (FIG. 6).

Exemplary Procedures

Figure 7:
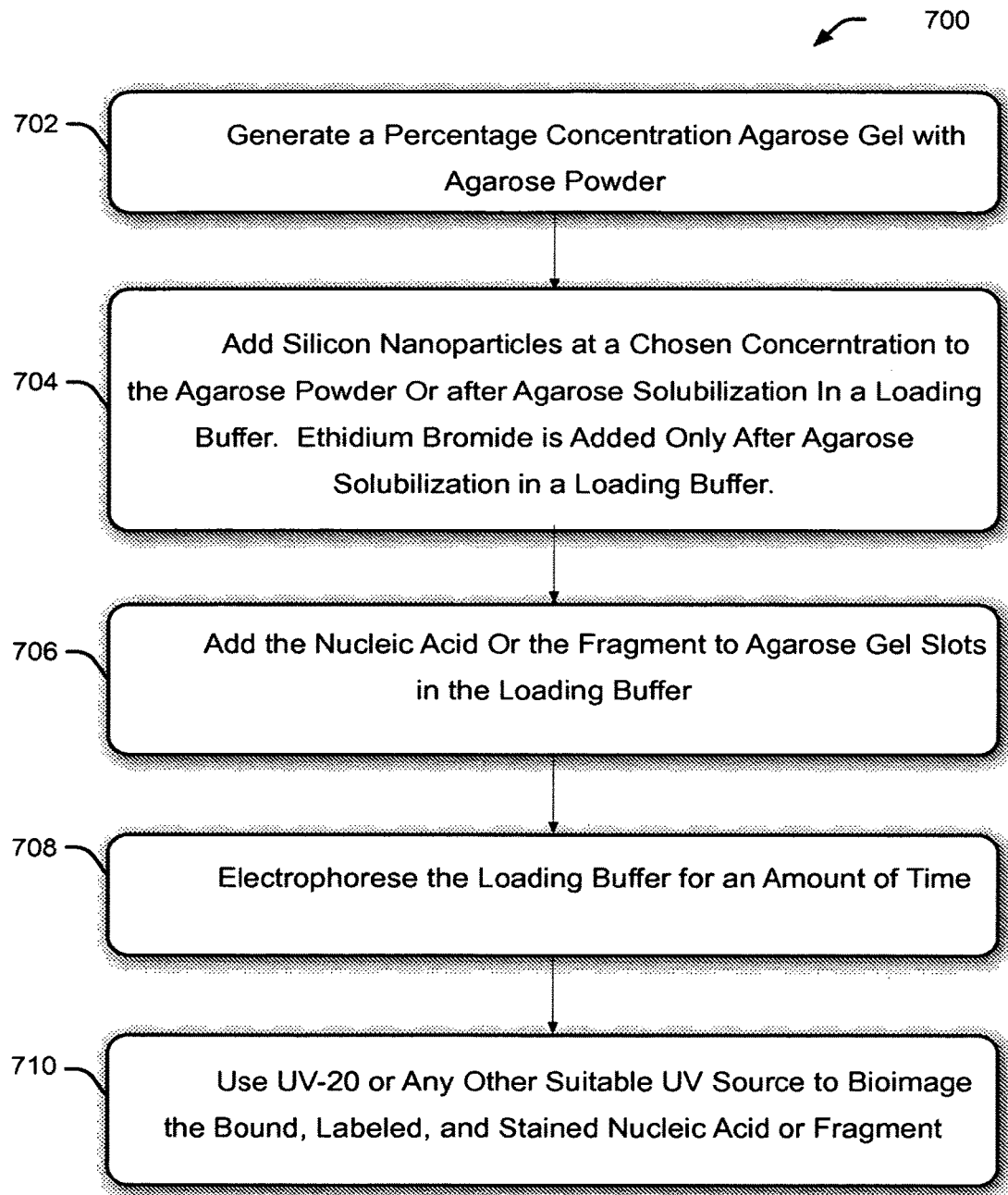
FIG. 7 illustrates an exemplary procedure for bioimaging nucleic acids, proteins or enzymes, according to one embodiment.

FIG. 7 illustrates an exemplary procedure for bioimaging nucleic acids and their fragments, according to one embodiment. The nucleic acid can be deoxyribonucleic acid (DNA) and where the fragment is one of genomic DNA, polymerase chain reaction products, DNA strands of different molecular weight, ribonucleic acid (RNA) or a fragment of it. Block 702 generates a percentage concentration agarose gel with agarose powder. In one implementation, the percentage concentration is 1% to 2.5% concentration in Sigma Tris-acetate-EDTA buffer (TAE) after 10× dilution.

Block 704 includes adding silicon nanoparticles at a chosen concentration to the agarose powder or after agarose solubilization in a loading buffer. Ethidium bromide is added only after agarose solubilization. In one implementation, the added silicon nanoparticles are 1 nm, 3 nm, 5 nm, or 25 nm in diameter. Block 706 adds the nucleic acid or the fragment to agarose gel slots in the loading buffer. Block 708 electrophoreses the loading buffer for an amount of time. The electrophoresing causes the added silicon nanoparticles or the added ethidium bromide to generate a bound, labeled, and stained nucleic acid or fragment by (a) binding the nucleic acid or the fragment, (b) labeling the nucleic acid or the fragment, and (c) staining the nucleic acid or the fragment for bioimaging visualization. In one implementation, the amount of time for electrophoresing the loading buffer is 45 minutes at 40 mA and 140 volts.

Block 710 uses an Ultra Violet (UV) lamp or microwave UV-20 or any other suitable UV source to bioimage the bound, labeled, and stained nucleic acid or fragment.

In one implementation, operations of procedure 700 are used to detect electrophoretic bands containing more than 5 ng of nucleic acids. Procedure 700 gives staining stability to the electrophoretic bands much higher than with ethidium bromide in agarose gel. This procedure can be used for bioimaging DNA, RNA and their fragments in situ in healthy and diseased tissue.

Figure 8:
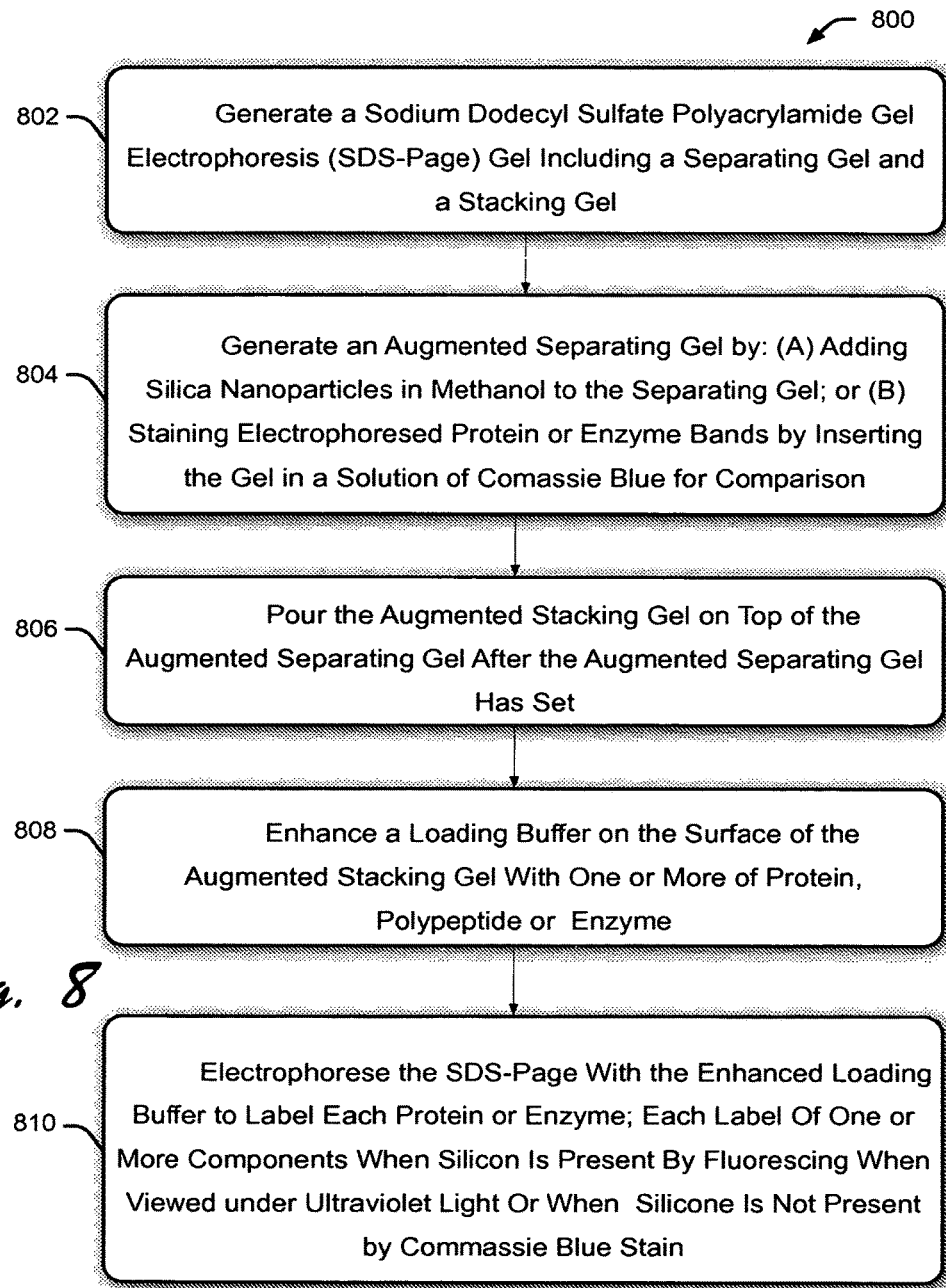
FIG. 8 shows an exemplary procedure to visualize a protein, polypeptide or enzyme, according to one embodiment.

FIG. 8 shows an exemplary procedure 800 to visualize a protein, polypeptide or enzyme, according to one embodiment. This procedure allows researchers in the various biological and medical fields to examine the electrophoretic proteins and enzymes patterns immediately after finishing electrophoretic runs. This is because in one implementation, there is no need to wait for staining with coomassie blue and destaining the excess dye.

At 802 the procedure 800 generates sodium dodecyl sulfate polyacrylamide gel electrophoresis (SDS-PAGE) gel including a separating gel and a stacking gel. In one implementation, the augmented stacking gel is in a concentration of 1% to 4%. In one implementation, generating the SDS-PAGE gel comprises preparing a 12.5% polyacrylamide separating gel in 0.375M Tris-HCl containing 0.1% SDS weight (of solute) per volume (of solvent) ("w/v"), 0.05% w/v ammonium persulphate and 0.03% volume (of solute) per volume (of solvent) ("v/v") tetramethylethylenediamine (TEMED), pH 8.8. In one implementation, generating the SDS-PAGE gel further comprises preparing a 4% stacking gel in 0.125M Tris-HCl, containing 0.1% SDS w/v, 0.05% w/v ammonium persulphate and 0.05% TEMED, pH 6.8.

In another implementation, generating the SDS-PAGE gel further includes: Preparing the stacking gel by: forming, before the stacking gel has set, one or more sample protein, polypeptide or enzyme wells on the stacking gel. In this scenario, the stacking gel with its one or more sample protein, polypeptide or enzyme wells is allowed to set at room temperature. In another implementation, generating the SDS-PAGE gel includes placing the stacking gel, with the one or more protein, polypeptide or enzyme wells that have set, into an electrophoreses tank in which the stacking gel is covered with a running buffer. In one embodiment, the running buffer is 25 mM Tris-HCl, 192 mM Glycine, 0.1% SDS, and pH 8.3.

At block 804, an augmented separating gel is generated by: (a) adding silicon nanoparticles in methanol to the separating gel; or (b) staining electrophoresed protein or enzyme bands, for the sake of comparison, with commassie blue. In one implementation, the silicon nanoparticles in methanol further comprises adding silicon nanoparticles in methanol at 976 µg/ml gel mix (1.16 µmol/ml). In another implementation, the adding the silicon nanoparticles in methanol further comprises adding 1 ng of silicon nanoparticles in methanol at 976 µg/ml gel mix (1.16 µmol/ml). In one implementation, the separating gel is in a concentration in a range of 7% to 12.5%. In one implementation, further comprising increasing the concentration and or size of used silicon nanoparticles to provide clearer electrophoretic bands.

At block 806, the augmented stacking gel is poured on top of the augmented separating gel after the augmented separating gel has set. Block 808 enhances a loading buffer on the surface of the augmented stacking gel with one or more protein, polypeptide or enzyme. In one implementation, the one or more protein, polypeptide or enzyme(s) are with varying molecular weights diluted with equal volume of a sample treatment buffer. Additionally, the procedure further comprises running the whole biphasic gels at a selected energy level until the tracking dye (bromophenol blue) entered the separating (resolving) gel, then for one and a half hours at an energy level greater than the selected energy level. In one embodiment of this latter implementation, the sample treatment buffer is 0.125M Tris-HCl, 4% SDS, 20% glycerol, 2% 2-mercaptoethanol, 0.03 mM bromophenol blue, with a pH 6.8, wherein the selected energy level is 15 mA, and where the energy level greater than the selected energy level is 20 mA.

Operations of block 810 electrophorese the SDS-PAGE with the enhanced loading buffer to label each protein or enzyme, each label of one or more components when silicon is present by fluorescing when viewed under ultra violet (UV) light, or when silicon is not present by commassie blue stain. In one implementation, and if silicon nanoparticles are present, the procedure comprises using an Ultra Violet (UV) lamp or microwave UV-20 or another UV light detector to bioimage a bound, and labeled nucleic acid fragment.

In one implementation, procedure 800 is independent of the augmented stacking gel. This embodiment includes separating and visualizing proteins, polypeptides or enzymes by loading them into slots situated on the surface of the separating gel.

Alternate Embodiments

Although exemplary systems and methods for labeling, staining, and bioimaging of nucleic acids, proteins, and enzymes have been described in language specific to structural features and/or methodological operations or actions, it is understood that the implementations defined in the appended claims are not necessarily limited to the specific features or actions described. Accordingly, the specific features and operations of the described systems and methods are disclosed as exemplary forms of implementing the claimed subject matter.

The invention claimed is:
1. A method comprising:
    visualizing by:
        (i) generating sodium dodecyl sulfate polyacrylamide gel electrophoresis (SDS-PAGE) gel including a separating gel and a stacking gel;
        generating an augmented separating gel by:

(a) adding silicon nanoparticles in methanol to the separating gel;

(ii) pouring an augmented stacking gel on top of the augmented separating gel after the augmented separating gel has set;

(iii) enhancing a loading buffer on the surface of the augmented stacking gel with one or more protein, polypeptide or enzyme; and (iv) electrophoresing the SDS-PAGE with the enhanced loading buffer to label each protein or enzyme, each label of one or more components by fluorescing when viewed under ultra violet (UV) light;

wherein visualizing is done to visualize a protein, polypeptide or an enzyme; and wherein generating the SDS-PAGE gel further comprises preparing a 12.5% polyacrylamide separating gel in 0.375M Tris-HC1 containing 0.1% SDS weight (of solute) per volume (of solvent) ("w/v"), 0.05% w/v ammonium persulphate and 0.03% volume (of solute) per volume (of solvent) ("v/v") tetramethylethylenediamine (TEMED), pH 8.8;

wherein generating the SDS-PAGE gel further comprises preparing a 4% stacking gel in 0.125M Tris-HC1, containing 0.1% SDS w/v, 0.05% w/v ammonium persulphate and 0.05% TEMED, pH 6.8;

wherein generating the SDS-PAGE gel further comprises: preparing the stacking gel by: forming, before the stacking gel has set, one or more sample protein, polypeptide or enzyme wells on the stacking gel; and allowing the stacking gel with its one or more sample protein, polypeptide or enzyme wells to set at room temperature;

wherein generating the SDS-PAGE gel further comprises placing the stacking gel, with the one or more protein, polypeptide or enzyme wells that have set, into an electrophoreses tank in which the stacking gel is covered with a running buffer; and wherein the running buffer is 25 mM Tris-HC1, 192 mM Glycine, 0.1% SDS, and pH 8.3; and wherein adding the silicon nanoparticles in methanol further comprises adding 1 ng silicon nanoparticles in methanol at 976 g/ml gel mix and 1.16 mol/ml;

wherein one or more articles being visualized have varying molecular weights diluted with equal volume of a sample treatment buffer; and wherein the method further comprises running whole biphasic gels at a selected energy level until a tracking dye, wherein the tracking dye is bromophenol blue, enters a separating resolving gel; and running the resolving gel for one and a half hours at an energy level greater than the selected energy level; and wherein one or more articles being visualized have varying molecular weights diluted with equal volume of a sample treatment buffer; and wherein the sample treatment buffer is 0.125M Tris-HC1, 4% SDS, 20% glycerol, 2% 2-mercaptoethanol, 0.03 mM bromophenol blue, with a pH 6.8, wherein the selected energy level is 15 mA, and where the energy level greater than the selected energy level is 20 mA; and further comprising separating and visualizing proteins, polypeptides or enzymes by loading them into slots situated on the surface of the separating gel;

wherein the augmented stacking gel is in a concentration of 1% to 4%; wherein the separating gel is in a concentration in a range of 7% to 12.5%;

the method further comprises using an Ultra Violet (UV) lamp or microwave UV-20 or another UV light detector to bioimage a bound, and labeled nucleic acid or a fragment of it; and further comprising increasing the concentration of used silicon nanoparticles to provide clearer electrophoretic bands.

* * * * *